United States Patent
Framroze et al.

(10) Patent No.: US 11,634,392 B2
(45) Date of Patent: Apr. 25, 2023

(54) PURIFICATION OF SULFENTRAZONE HERBICIDE USING SELECTIVE PH ADJUSTED EXTRACTIONS

(71) Applicant: Tagros Chemicals India Pvt Ltd, Tamil Nadu (IN)

(72) Inventors: Bomi P Framroze, Portola Valley, CA (US); Rajaiah Shrikrishnan, Chennai (IN); Rajagopal Kuppuswamy, Chennai (IN)

(73) Assignee: Tagros Chemicals India Pvt Ltd, Chennai (IN)

( * ) Notice: Subject to any disclaimer, the term of this patent is extended or adjusted under 35 U.S.C. 154(b) by 108 days.

(21) Appl. No.: 17/064,447

(22) Filed: Oct. 6, 2020

(65) Prior Publication Data

US 2022/0106277 A1 Apr. 7, 2022

(51) Int. Cl.
*C07D 249/08* (2006.01)
*B01D 3/40* (2006.01)
*A01N 43/653* (2006.01)
*C07B 63/00* (2006.01)

(52) U.S. Cl.
CPC ......... *C07D 249/08* (2013.01); *A01N 43/653* (2013.01); *B01D 3/40* (2013.01); *C07B 63/00* (2013.01)

(58) Field of Classification Search
CPC .................................................. C07D 249/08
See application file for complete search history.

(56) References Cited

U.S. PATENT DOCUMENTS

| | | | |
|---|---|---|---|
| 4,818,275 A | 4/1989 | Theodoridis | |
| 5,990,315 A * | 11/1999 | Dumas | C07D 249/12 548/263.2 |

FOREIGN PATENT DOCUMENTS

| | | |
|---|---|---|
| CN | 108424395 B | 7/2021 |
| WO | WO-2019141230 A1 | 7/2019 |

* cited by examiner

*Primary Examiner* — Shawquia Jackson
(74) *Attorney, Agent, or Firm* — Schwegman Lundberg & Woessner, P.A.

(57) ABSTRACT

A high yielding extraction process for the purification of N-(2,4-dichloro-5-(4-(difluoromethyl)-3-methyl-5-oxo-4,5-dihydro-1H-1,2,4-triazol-1-yl)methanesulfonamide (sulfentrazone) by selectively partitioning the desired product from the crude mixture, thereby increasing its purity by decreasing the presence of unwanted impurities and improving the color and particle size distribution of the final sulfentrazone product. The selective partitioning is achieved by the sequential use of an organic solvent, water, aqueous inorganic base and a concentrated aqueous inorganic acid.

4 Claims, No Drawings

PURIFICATION OF SULFENTRAZONE HERBICIDE USING SELECTIVE PH ADJUSTED EXTRACTIONS

FIELD

This invention relates to a high yielding extraction process for the purification of N-(2,4-dichloro-5-(4-(difluoromethyl)-3-methyl-5-oxo-4,5-dihydro-1H-1,2,4-triazol-1-yl) methanesulfonamide (sulfentrazone) by selectively partitioning the desired product from the crude mixture, thereby increasing its purity by decreasing the presence of unwanted impurities and improving the color and particle size distribution of the final sulfentrazone product in high yield.

BACKGROUND

N-(2,4-dichloro-5-(4-(difluoromethyl)-3-methyl-5-oxo-4, 5-dihydro-1H-1,2,4-triazol-1-yl) methanesulfonamide (sulfentrazone) is an important commercial herbicide in agriculture. The synthesis of sulfentrazone has been described in many publications such as, U.S. Pat. Nos. 4,818,275, 5,990,315, WO2019141230A1, CN108424395A and references cited therein. In all of these publications, the sulfentrazone produced is described at purity levels between 85% and 95% by various analytical methods. Further the product produced by synthesis routes described in the art are colored brown to dark beige and the consistency of the powder produced is described variously as granular and lumpy.

Further purification of sulfentrazone to arrive at greater than 95% purity is carried out by various recrystallization processes, as described in the art. The purification of sulfentrazone and the removal of impurities is particularly necessary since several of these impurities are undesired due to their potential to cause injury to off-target crops or their unnecessary persistence in the environment. Of particular mention are the impurities, 2-(5-amino-2,4-dichlorophenyl)-4-(difluoromethyl)-5-methyl-2,4-dihydro-3H-1,2,4-triazol-3-one (the precursor compound to sulfentrazone); N-{4-chloro-3-[4-(difluoromethyl)-3-methyl-5-oxo-4,5-dihydro-1H-1,2,4-triazol-1-yl]phenyl}methanesulfonamide (the mono chloro analog of sulfentrazone and 1-(5-Amino-2-chlorophenyl)-4-(difluoromethyl)-3-methyl-1H-1,2,4-triazol-5(4H)-one (its precursor compound). The recrystallizations described in the art often lead to significant loss of yield and large quantities of effluents while still producing variable color and consistency of powder.

Consequently there still exists a need for a commercially viable method to produce sulfentrazone; in greater than 95% purity, with significantly lower or with the total absence of key impurities, with an white to off-white color and with a uniform consistency of particle size without lumps and coagulations, so as to be in a form suitable to produce stable commercial formulations for use in herbicidal agricultural applications.

SUMMARY OF THE INVENTION

The present invention describes a high yielding extraction process for the purification of N-(2,4-dichloro-5-(4-(difluoromethyl)-3-methyl-5-oxo-4,5-dihydro-1H-1,2,4-triazol-1-yl) methanesulfonamide (sulfentrazone) by selectively partitioning the desired product from the crude production mixture, and increasing its overall purity by decreasing the presence of unwanted impurities while improving the color and particle size distribution of the final sulfentrazone product. This selective partitioning is achieved by the sequential use of an organic solvent, water, aqueous sodium carbonate and a concentrated inorganic acid.

The prior art does not describe any process for the purification of sulfentrazone by use of a selective extraction process that uses an aqueous base and acid together with an organic solvent to purify sulfentrazone. Quite contrary, the literature describes sulfentrazone as a non-charged neutral pH compound and one that is not likely to partition into a basic aqueous solution. Hence no such partitioning of sulfentrazone into a basic pH aqueous system has been described in the literature.

In the present invention, a solution of 1-(5-amino-2,4-dichlorophenyl)-4-(difluoromethyl)-3-methyl-1H-1,2,4-triazol-5(4H)-one is dehydrated using toluene and reacted with methanesulfonyl chloride in the presence of pyridine. After completion of the reaction, the toluene is removed by distillation and replaced with ethylene dichloride. Water is added and the mixture stirred. After the stirring is stopped the layers are separated and the ethylene dichloride layer is set for distillation to remove 70 percent to 90 percent of the ethylene dichloride. Further water is added and the mass heated to 65° C. To this is added an aqueous solution of sodium carbonate and after further heating and stirring is slowly added an aqueous solution of concentrated hydrochloric acid. After subsequent stirring, N-(2,4-dichloro-5-(4-(difluoromethyl)-3-methyl-5-oxo-4,5-dihydro-1H-1,2,4-triazol-1-yl)methanesulfonamide (sulfentrazone) precipitates out of the solution which is collected and dried, The yield of sulfentrazone is 90 percent, the purity 99.4 percent and the total impurities are less than 0.6 percent, by GC analysis.

Thus the method described herein uses the hitherto unknown use of an n-chloroalkyl solvent, an aqueous inorganic base and an aqueous inorganic acid in a partitioning extraction sequence to purify sulfentrazone to greater than 99 percent purity and with a desirable pale brown to white color and a consistent particle size with no lumps or agglomerates.

This new method also eliminates the need for wasteful recrystallization or other expensive chromatographic separation techniques to produce the commercially desired greater than or equal to 99 percent pure sulfentrazone.

DETAILED DESCRIPTION OF THE INVENTION

Before describing the present invention in detail, it is to be understood that the terminology used herein is for the purpose of describing particular embodiments only, and is not intended to be limiting.

In accordance with the present invention, there is provided a process to produce a high purity sulfentrazone in a highly cost effective manner.

It will be clear to those skilled in the art that modifications can be made to the process described herein without departing from the inventive concept set forth in our claims below.

Example-1

Step A-1 Synthesis of crude N-(2,4-dichloro-5-(4-(difluoromethyl)-3-methyl-5-oxo-4,5-dihydro-1H-1, 2,4-triazol-1-yl)methanesulfonamide A stirred solution of 148 grams of 1-(5-amino-2,4-dichlorophenyl)-4-(difluoromethyl)-3-methyl-1H-1,2,4-triazol-5

(4H)-one (0.478 moles) in 592 ml of toluene was heated to reflux at 110-115° C. for one hour to remove the moisture azeotropically. 200 ml of toluene was recovered during the dehydration. The reaction mass was cooled to 85-90° C. over a period of 30-45 minutes and 43.4 grams of pyridine (0.549 mole) was added over a period of 30 minutes. The addition of pyridine was followed by dropwise addition of 70.8 grams of methanesulfonyl chloride (0.623 mole) over a period of 3 hours by maintaining the mass temperature at 85-90° C. and continued to cook the reaction mass at 85-90° C. for a period of 2 hours. After completion of reaction, the reaction mass was cooled to 75-80° C. and solvent toluene was distilled under vacuum. After completion of toluene recovery 625 ml of solvent ethylene dichloride and 260 ml of water was added to the kettle and stirred for 15 minutes. Then layers were separated. The ethylene dichloride layer was distilled to remove 80% of ethylene dichloride to get the crude product, N-(2,4-dichloro-5-(4-(difluoromethyl)-3-methyl-5-oxo-4,5-dihydro-1H-1,2,4-triazol-1-yl) methanesulfonamide. Purity=94.6%; Total Impurities 5.6% as shown in Table 1 below.

TABLE 1

List of impurities in Crude product N-(2,4-dichloro-5-(4-(difluoromethyl)-3-methyl-5-oxo-4,5-dihydro-1H-1,2,4-triazol-1-yl) methanesulfonamide

| No | Name of the impurities | Structure | Impurity Percent |
|---|---|---|---|
| 1 | 1-(5-Amino-2-chlorophenyl)-4-(difluoromethyl)-methyl-1H-1,2,4-triazol-5(4H)-one | 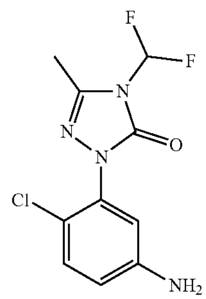 [SMILES: Cc1nn(-c2cc(N)ccc2Cl)c(=O)n1C(F)F] | 0.5 |
| 2 | N,N'-((4,4'-(ethane-1,2-diyl)bis(3-methyl-5-oxo-4,5-dihydro-1H-1,2,4-triazole-4,1-diyl))bis(2,4-dichloro-5,1-phenylene)) dimethanesulfonamide (DMSF) | 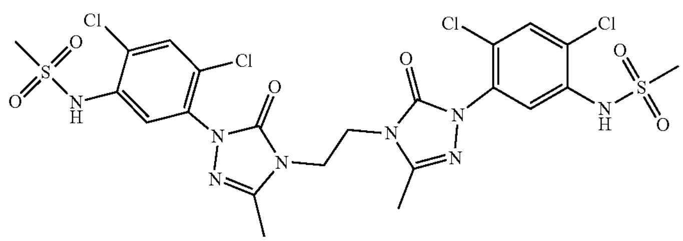 | 0.2 |
| 3 | N-{4-chloro-3-[4-(difluoromethyl)-3-methyl-5-oxo-4,5-dihydro-1H-1,2,4-triazol-1-yl]phenyl} methane sulfonamide | 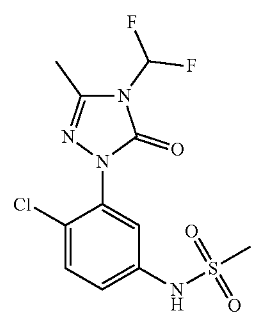 [SMILES: Cc1nn(-c2cc(NS(C)(=O)=O)ccc2Cl)c(=O)n1C(F)F] | 0.5 |
| 4 | 1-(3-aminophenyl)-4-(difluoromethyl)-3-methyl-1H-1,2,4-triazol-5(4H)-one | 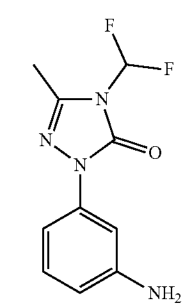 | 0.3 |

TABLE 1-continued

List of impurities in Crude product N-(2,4-dichloro-5-(4-(difluoromethyl)-3-methyl-5-oxo-4,5-dihydro-1H-1,2,4-triazol-1-yl)methanesulfonamide

| No | Name of the impurities | Structure | Impurity Percent |
|----|------------------------|-----------|------------------|
| 5 | 2-(5-amino-2,4-dichlorophenyl)-4-(difluoromethyl)-5-methyl-2,4-dihydro-3H-1,2,4-triazol-3-one | 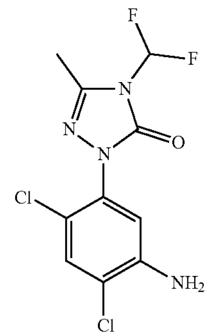 [SMILES: Cc1nn(-c2cc(N)c(Cl)cc2Cl)c(=O)n1C(F)F] | 3.0 |
| 6 | N-(3-(4-(difluoromethyl)-3-methyl-5-oxo-4,5-dihydro-1H-1,2,4-triazol-1-yl)phenyl)methanesulfonamide | 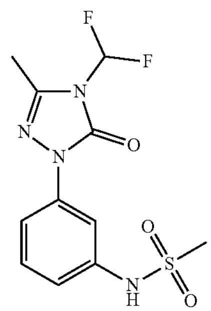 | 0.3 |
| 7 | N-(3-(4-(difluoromethyl)-3-methyl-5-oxo-4,5-dihydro-1H-1,2,4-triazol-1-yl)phenyl)-N-(methylsulfonyl)methanesulfonamide | 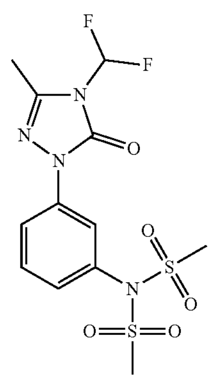 | 0.4 |
| 8 | Toluene | 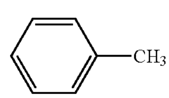 | 3.0 |

Step A-2 Purification of crude N-(2,4-dichloro-5-(4-(difluoromethyl)-3-methyl-5-oxo-4,5-dihydro-1H-1,2,4-triazol-1-yl)methanesulfonamide Charged 1075 ml of water under stirring and the crude mass and was heated to 60-65° C. 226.2 ml of 20% sodium carbonate solution (54.2 grams of sodium carbonate dissolved in 212 ml of water) was added under stirring over a period of 1 hour and further maintained the reaction mass at 60-65° C. for a period of 1.5 hours. Followed by the addition of 20% sodium carbonate solution, 90 ml of concentrated hydrochloric acid (30% strength) was added dropwise over a period of 3-4 hours at 60-65° C. The mass was stirred for 30 minutes. The precipitated solid was collected by filtration and washed with water. The dried solid weighed 166.6 grams of N-(2,4-dichloro-5-(4-(difluoromethyl)-3-methyl-5-oxo-4,5-dihydro-1H-1,2,4-triazol-1-yl) methanesulfonamide with yield 90% and purity 99.4%; Total Impurities 0.6% as shown in Table 2 below.

TABLE 2

List of impurities in purified compound N-(2,4-dichloro-5-(4-(difluoromethyl)-3-methyl-5-oxo-4,5-dihydro-1H-1,2,4-triazol-1-yl)methanesulfonamide

| No. | Name of the impurities | Structure | Impurities Percent |
|-----|------------------------|-----------|--------------------|
| 1 | 1-(5-Amino-2-chlorophenyl)-4-(difluoromethyl)-3-methyl-1H-1,2,4-triazol-5(4H)-one | 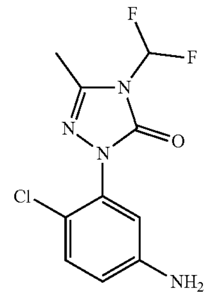 [SMILES: Cc1nn(-c2cc(N)ccc2Cl)c(=O)n1C(F)F] | Nil |
| 2 | N,N'-((4,4'-(ethane-1,2-diyl)bis(3-methyl-5-oxo-4,5-dihydro-1H-1,2,4-triazole-4,1-diyl))bis(2,4-dichloro-5,1-phenylene))dimethanesulfonamide (DMSF) | 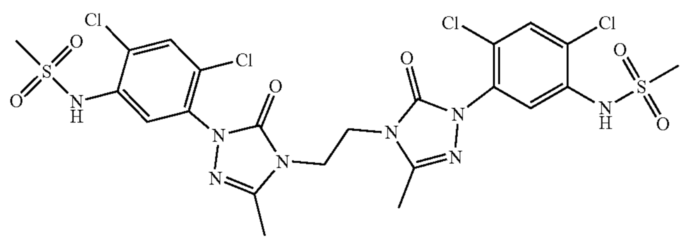 [SMILES: Cc1nn(-c2cc(NS(C)(=O)=O)c(Cl)cc2Cl)c(=O)n1CCn1c(C)nn(-c2cc(NS(C)(=O)=O)c(Cl)cc2Cl)c1=O] | Nil |
| 3 | N-{4-chloro-3-[4-(difluoromethyl)-3-methyl-5-oxo-4,5-dihydro-1H-1,2,4-triazol-1-yl]phenyl}methane sulfonamide | 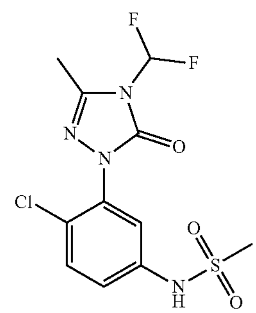 [SMILES: Cc1nn(-c2cc(NS(C)(=O)=O)ccc2Cl)c(=O)n1C(F)F] | 0.1 |
| 4 | 1-(3-aminophenyl)-4-(difluoromethyl)-3-methyl-1H-1,2,4-triazol-5(4H)-one | 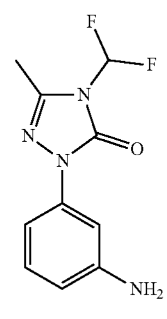 [SMILES: Cc1nn(-c2cccc(N)c2)c(=O)n1C(F)F] | Nil |
| 5 | 2-(5-amino-2,4-dichloro phenyl)-4-(difluoromethyl)-5-methyl-2,4-dihydro-3H-1,2,4-triazol-3-one | 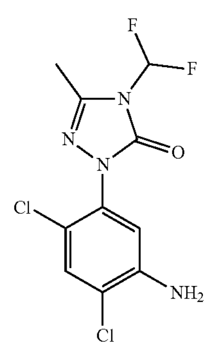 [SMILES: Cc1nn(-c2cc(N)c(Cl)cc2Cl)c(=O)n1C(F)F] | 0.3 |

TABLE 2-continued

List of impurities in purified compound N-(2,4-dichloro-5-(4-(difluoromethyl)-3-methyl-5-oxo-4,5-dihydro-1H-1,2,4-triazol-1-yl)methanesulfonamide

| No. | Name of the impurities | Structure | Impurities Percent |
|-----|------------------------|-----------|--------------------|
| 6 | N-(3-(4-(difluoromethyl)-3-methyl-5-oxo-4,5-dihydro-1H-1,2,4-triazol-1-yl)phenyl)methanesulfonamide | [structure] | Nil |
| 7 | N-(3-(4-(difluoromethyl)-3-methyl-5-oxo-4,5-dihydro-1H-1,2,4-triazol-1-yl)phenyl)-N-(methylsulfonyl)methanesulfonamide | [structure] | 0.2 |
| 8 | Toluene | [structure] | Nil |

Example 2

The crude compound N-(2,4-dichloro-5-(4-(difluoromethyl)-3-methyl-5-oxo-4,5-dihydro-1H-1,2,4-triazol-1-yl)methanesulfonamide was prepared in the manner of Example 1 Step A-1. Purification was performed using the same procedure as Example 1 Step A-2 except substituting concentrated hydrochloric acid with 50 ml of 50% aqueous sulfuric acid. The weight of purified N-(2,4-dichloro-5-(4-(difluoromethyl)-3-methyl-5-oxo-4,5-dihydro-1H-1,2,4-triazol-1-yl) methanesulfonamide was 160.1 grams corresponding to an yield of 86.5%. Purity=98.4%. Total Impurities=1.6%

Example 3

The crude compound N-(2,4-dichloro-5-(4-(difluoromethyl)-3-methyl-5-oxo-4,5-dihydro-1H-1,2,4-triazol-1-yl)methanesulfonamide was prepared in the manner of Example 1, Step A-1. Purification was performed using the same procedure as Example 1 Step A-2 except substituting aqueous sodium carbonate solution with 330 ml of 20% aqueous potassium carbonate solution. The weight of purified N-(2,4-dichloro-5-(4-(difluoromethyl)-3-methyl-5-oxo-4,5-dihydro-1H-1,2,4-triazol-1-yl) methanesulfonamide was 159.9 grams corresponding to an yield of 86.4%. Purity=99.2%. Total Impurities=0.8%

Example 4

The crude compound N-(2,4-dichloro-5-(4-(difluoromethyl)-3-methyl-5-oxo-4,5-dihydro-1H-1,2,4-triazol-1-yl) methanesulfonamide was prepared in the manner of Example 1, Step A-1. Purification was performed using the same procedure as Example 1 Step A-2 except substituting aqueous sodium carbonate solution with 330 ml of 20% aqueous potassium carbonate solution and the concentrated hydrochloric acid with 50 ml of 50% aqueous sulfuric acid. The weight of purified N-(2,4-dichloro-5-(4-(difluoromethyl)-3-methyl-5-oxo-4,5-dihydro-1H-1,2,4-triazol-1-yl) methanesulfonamide was 153.6 grams corresponding to an yield of 83.0%. Purity=99.6%. Total Impurities=0.4%

Example 5

The crude compound N-(2,4-dichloro-5-(4-(difluoromethyl)-3-methyl-5-oxo-4,5-dihydro-1H-1,2,4-triazol-1-yl) methanesulfonamide was prepared in the manner of Example 1, Step A-1. Purification was performed using the same procedure as Example 1 Step A-2 except substituting aqueous sodium carbonate solution with 330 ml of 20% aqueous potassium hydroxide solution. The weight of purified N-(2,4-dichloro-5-(4-(difluoromethyl)-3-methyl oxo-4,5-dihydro-1H-1,2,4-triazol-1-yl) methanesulfonamide was 145.5 grams corresponding to an yield of 78.6%. Purity=99.1%. Total Impurities=0.9%

Example 6

The crude compound N-(2,4-dichloro-5-(4-(difluoromethyl)-3-methyl-5-oxo-4,5-dihydro-1H-1,2,4-triazol-1-yl) methanesulfonamide was prepared in the manner of Example 1, Step A-1. Purification was performed using the same procedure as Example 1 Step A-2 except substituting aqueous sodium carbonate solution with 330 ml of 20% aqueous potassium hydroxide solution and the concentrated hydrochloric acid with 50 ml of 50% aqueous sulfuric acid. The weight of purified N-(2,4-dichloro-5-(4-(difluoromethyl)-3-methyl-5-oxo-4,5-dihydro-1H-1,2,4-triazol-1-yl) methanesulfonamide was 142.5 grams corresponding to an yield of 77.0%. Purity=99.1%. Total Impurities=0.9%

Example 7

The crude compound N-(2,4-dichloro-5-(4-(difluoromethyl)-3-methyl-5-oxo-4,5-dihydro-1H-1,2,4-triazol-1-yl) methanesulfonamide was prepared in the manner of Example 1, Step A-1. Purification was performed using the same procedure as Example 1 Step A-2 except substituting aqueous sodium carbonate solution with 96 ml of 20% aqueous sodium hydroxide solution. The weight of purified N-(2,4-dichloro-5-(4-(difluoromethyl)-3-methyl-5-oxo-4,5-dihydro-1H-1,2,4-triazol-1-yl) methanesulfonamide was 138.8 grams corresponding to an yield of 75.0%. Purity=99.3%. Total Impurities=0.7%

Example 8

The crude compound N-(2,4-dichloro-5-(4-(difluoromethyl)-3-methyl-5-oxo-4,5-dihydro-1H-1,2,4-triazol-1-yl) methanesulfonamide was prepared in the manner of Example 1, Step A-1. Purification was performed using the same procedure as Example 1 Step A-2 except substituting aqueous sodium carbonate solution with 96 ml of 20% aqueous sodium hydroxide solution and the concentrated hydrochloric acid with 50 ml of 50% aqueous sulfuric acid. The weight of purified N-(2,4-dichloro-5-(4-(difluoromethyl)-3-methyl-5-oxo-4,5-dihydro-1H-1,2,4-triazol-1-yl) methanesulfonamide was 135.1 grams corresponding to an yield of 73.0%. Purity=99.0%. Total Impurities=1.0%

Example 9

The crude compound N-(2,4-dichloro-5-(4-(difluoromethyl)-3-methyl-5-oxo-4,5-dihydro-1H-1,2,4-triazol-1-yl) methanesulfonamide was prepared in the manner of Example 1, Step A-1.

Purification was performed using the same procedure as Example 1 Step A-2 except substituting aqueous sodium carbonate solution with 213 ml of 20% aqueous sodium bicarbonate solution. The weight of purified N-(2,4-dichloro-5-(4-(difluoromethyl)-3-methyl oxo-4,5-dihydro-1H-1,2,4-triazol-1-yl) methanesulfonamide was 129.6 grams corresponding to an yield of 70.0%. Purity=98.0%. Total Impurities=2.0%

What is claimed is:

1. A process that increases the purity of N-(2,4-dichloro-5-(4-(difluoromethyl)-3-methyl-5-oxo-4,5-dihydro-1H-1,2,4-triazol-1-yl)phenyl)methanesulfonamide by a sequential extraction process:
    i. By initially contacting the crude N-(2,4-dichloro-5-(4-(difluoromethyl)-3-methyl-5-oxo-4,5-dihydro-1H-1,2,4-triazol-1-yl)phenyl)methanesulfonamide with a mixture of n-chloroalkyl organic solvent and water;
    ii. Separating the n-chloroalkyl organic solvent layer from the water layer;
    iii. Removing more than 75 percent by volume of the n-chloroalkyl solvent by distillation;
    iv. Adding an aqueous inorganic base of pH between 11 and 12;
    v. Adding an aqueous inorganic acid of pH less than or equal to 1; and
    vi. Filtering and drying the resultant precipitated solid N-(2,4-dichloro-5-(4-(difluoromethyl)-3-methyl-5-oxo-4,5-dihydro-1H-1,2,4-triazol-1-yl)phenyl)methanesulfonamide.

2. A process according to claim 1 wherein the n-chloroalkyl organic solvent is ethylene dichloride.

3. A process according to claim 1 wherein the aqueous inorganic base is sodium carbonate.

4. A process according to claim 1, wherein the aqueous inorganic acid is hydrochloric acid.

* * * * *